United States Patent [19]

Botta et al.

[11] Patent Number: 4,950,817

[45] Date of Patent: Aug. 21, 1990

[54] PROCESS FOR THE PREPARATION OF 4,4′-DIHALOBIPHENYLS

[75] Inventors: Artur Botta; Hans-Josef Buysch, both of Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 318,087

[22] Filed: Mar. 2, 1989

[30] Foreign Application Priority Data

Mar. 19, 1988 [DE] Fed. Rep. of Germany ....... 3809258
Jun. 14, 1988 [DE] Fed. Rep. of Germany ....... 3820192

[51] Int. Cl.$^5$ ..................... C07C 17/12; C07C 25/18
[52] U.S. Cl. .................................. 570/208; 570/206
[58] Field of Search ............................. 570/206, 208

[56] References Cited

U.S. PATENT DOCUMENTS 4,724,269 2/1988 Suzuki et al. ..................... 570/208

FOREIGN PATENT DOCUMENTS 2155009A 9/1985 United Kingdom ................ 570/206

OTHER PUBLICATIONS

Chen et al., *Chemical Engineering Progress*, Feb. 1988, pp. 32–40.

Primary Examiner—Werren B. Lone
Attorney, Agent, or Firm—Sprung Horn Kramer & Woods

[57] ABSTRACT

4,4′-dihalobiphenyls can be prepared by catalyzed halogenation of biphenyls with halogenating agents, the catalysts used being zeolites having pore sizes of at least 5 Å.

17 Claims, No Drawings

PROCESS FOR THE PREPARATION OF 4,4'-DIHALOBIPHENYLS

BACKGROUND OF THE INVENTION

The invention relates to a process for the preparation of 4,4'-dihalobiphenyls by selective halogenation o biphenyls in the presence of zeolites as catalysts having pore sizes of at least 5 Å.

4,4'-Dichloro- and -dibromobiphenyl are of great interest, for example as intermediates for the preparation of highly heat-resistant plastics, such as modified polyphenylene sulphide (cf. JP Patent Application No. 61/231,030 or U.S. Pat. No. 3,396,110 [C.A. 69 P 60 564 w]).

The conventional chlorination of biphenyl in the presence of Lewis acids leads to an unselective random substitution, in which the 4,4'derivative is not the preferred one. Thus, chlorination at 100° C. in the presence of 2.5% of FeCl3 produces a selectivity of only 8% of the 4,4'-dichloro isomer; the percentage of trichlorobiphenyl at 15% is remarkably high, the polychlorinated biphenyls belonging to the classes of the highly toxic substances as is known. According to the data of U.S. Pat. Nos. 1,946,040, 3,226,447 and GB No. 1,153,746, the addition of a sulphur compound in the chlorination of benzenes is intended to increase the selectivity in favour of the para-substitution. However, as shown by Comparative Example III below, the selectivity in favour of the 4,4'-dichlorobiphenyl in the chlorination of biphenyl is increased only insignificantly by the addition of 2.5% by weight of thiophene in addition to 2.5% by weight of FeCl3, while polychlorinated biphenyls at more than 9% by weight of the reaction product still constitute a significant percentage.

In practical application, the use of Lewis acids furthermore leads to increased problems with corrosion, as is known, and also to a more complicated workup and disposal.

SUMMARY OF THE INVENTION

A process for (he preparation of 4,4 -dihalobiphenyls of the formula

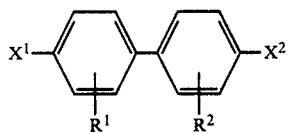
(I)

by catalyzed halogenation of biphenyls of the formula

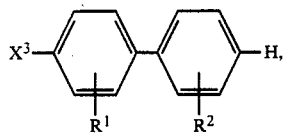
(II)

in which in the formula $X^1$ and $X^2$ independently of one another stand for chlorine, bromine or iodine, preferably for chlorine or bromine, particularly preferably for chlorine, $X^3$ stands for hydrogen, chlorine, bromine or iodine, preferably for hydrogen, chlorine or bromine, particularly preferably for hydrogen or chlorine, very particularly preferably for hydrogen and $R^1$ and $R^2$ independently of one another denote hydrogen, $C_1$-$C_4$-alkyl (preferably $C_1$-$C_2$-alkyl, particularly preferably methyl), $C_1$-$C_4$-alkoxy (preferably $C_1$-$C_2$-alkoxy, particularly preferably methoxy), hydroxyl, fluorine, chlorine or bromine, has now been found, which is characterized in that the biphenyls are reacted with halogenating agents in the presence of zeolites of the formula $$M_{m/z}[mMe^1O_2.nMe^2O_2].q\ H_2) \quad (III)$$

in which

M denotes an exchangeable cation, z denotes the valence of the cation, $Me^1$ and $Me^2$ represent the elements of the anionic skeleton, n/m denotes the ration of the elements and adopts a value of at least 1 and q denotes the amount of the water adsorbed, the zeolites having pore sizes of at least 5 Å.

DETAILED DESCRIPTION OF THE INVENTION

The process according to the invention accordingly allows the use of the biphenyls mentioned, it being possible for one of the para-positions to be already occupied by halogen; this last-mentioned variation even makes it possible to prepare biphenyls which are halogenated in the 4,4'-position with different halogens. Particularly preferably, the unsubstituted biphenyl is reacted. Using the unsubstituted biphenyl, the reaction according to the invention can be illustrated by the following formula scheme:

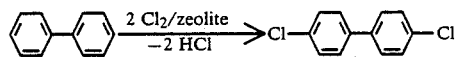

A high selectivity of the 4,4'-dihalogenation could not be expected according to the prior art. It is that the para-monochlorination of benzenes which are exclusively substituted by chlorine, lower alkyl or lower alkoxy in the presence of faujasite or zeolite L has been described (EP 112,722, EP 118,851, Stud. Surf. Sci. Catal. (Amsterdam) 28 (1986) 747–754), somewhat higher selectivities having been given for the para-chlorination. However, a bishalogenation of 2-ring aromatics in the presence of zeolites has hitherto not been described, because obviously a prejudice had to be overcome. The reason is that the monochlorination mentioned of benzenes using zeolites shifts the ortho-/para ratio from 1.1 in the conventional chlorination only down to 0.68 in the chlorination using zeolites, as was found by repeating the experiment. In view of the increased number of possible substitution patterns in the case of biphenyl, these results had to be considered completely inadequate and are in any case absolutely unsuitable to explain the large improvement of the 4,4' selectivity from 8% (conventional chlorination) to over 80% (chlorination according lo the invention). This achievement of the process according lo the invention is therefore entirely suprising.

Examples of starting materials for the process according to the invention in addition to the unsubstituted biphenyl are methyl-, dimethyl-, ethyl-, iso- propyl-, hydroxy- and methoxybiphenyl. For the preparation of asymmetric 4,4'-dihalobiphenyls such as for example, 4-bromo-4'-chlorobiphenyl, 4-chloro-4'-fluorobiphenyl or 4-chlor-4'-iodobiphenyl, 4-chloro-, 4-fluoro-, 4-bromo- or 4-iodo-biphenyl can be used as starting material.

Suitable halogenating agents are $Cl_2$, $Br_2$, $I_2$, $SO_2Cl_2$, $SO_2Br_2$, N-chloro- and N-bromosuccinimide and also bromine fluoride and bromine chloride. Preferably, $Cl_2$ or $Br_2$ are used. As a rule, the halogenating agent is used in a stoichiometric ratio with respect to the biphenyl, that is, in the case of not yet halogenated biphenyls in a molar ratio of 2:1, in the case of already monohalogenated biphenyls in a molar ratio of 1:1. It is possible to depart from this stoichiometric ratio by up to plus or minus 35 mole %, preferably up to 20 mol %.

The process according to the invention is carried out in the presence of zeolites as catalysts. Zeolites are crystalline alumosilicates which are composed of a network of $SiO_4$ or $AlO_4$ tetrahedra. The individual tetrahedra are connected to one another at the edges by means of oxygen bridges and form a three-dimensional network permeated by channels and void spaces. To balance the negative charge of the lattice, exchangeable cations are incorporated.

Si and Al in the zeolites can be replaced at least partially by other elements so that the zeolites can be described by the abovementioned formula (III).

A detailed description of zeolites is given, for example, in the monograph by D. W. Breck "Zeolite Molecular Sieves, Structure Chemistry and Use", J. Wiley and Sons, New York, 1964. Zeolites which are suitable for the process according to the invention have pore sizes of at least 5 Å, for example in the range from 5-Å, preferably 5-7 Å, and have an n/m ratio of 1-3,000, preferably 1-2,000. In formula (III), $Me^1$ denotes a trivalent element such as, for example, Al, Ga, In, B, V. Likewise, $Me^1$ can be an element such as P As Sb or Bi.

Preferably, $Me^1$ is a trivalent element, very particularly preferably Al by itself. $Me^2$ is at least partly Si, but in addition it can also be another tetravalent element such as, for example, Ti, Zr Hf, preferably $Me^2$ is only Si.

Particularly suitable zeolites, for example, are those of the structure type faujasite, L, offretite, gmelinite, cancrinite, H, ZSM 12, ZSM 25, zeolite β, ferrierite, ZSM 5, ZSM 11, heulandite, ZSM 22, ZSM 23, ZSM 48, ZSM 43, ZSM 35, PSH-3, zeolite ρ, ZSM 38, CSZ-1, XSM 3, ZSM 20, mordenite, zeolite-Ω, eronite, boron silicate, particularly preferably zeolites of the structure type mordenite, ferrierite, H, L,Ω, ZSM 11 or ZSM 5, very particularly preferably of the structure Ω or L.

The zeolite types mentioned can be supplied with exchangeable cations resulting from their synthesis or any variety of other cations in the context of an ion-exchange. This exchange is prior art and well known to one skilled in the art. According to the invention, suitable zeolite are not only those in their H form but also zeolites in which hydrogen has been replaced completely or partly for metal cations, for example for alkali metal ions, preferably $Na^+$ or $k^+$. In many cases, those forms in which hydrogen has been replaced partly or completely for two different metal cations, for example for the combination Na/K, are also suitable. The particularly preferred structure type L can contain, for example, cations of H, Na, K or mixtures thereof, preferably of Na, K or mixtures thereof, particularly preferably of K.

The zeolite catalyst is used in an amount of 1–100% by weight, preferably 5–50% by weight, particularly preferably 10–30% by weight, relative to the weight of the biphenyl to be reacted.

Furthermore, it has been found that the selectivity of the zeolite catalyst can be increased by cocatalysts. Co-catalysts are polar substances which can supposedly interact with active centres of the zeolite catalyst. Co-catalysts belong, for example, to the following group: water, alcohols, aldehydes or acetals thereof, ketones, carboxylic acids or salts thereof, halides thereof, amides thereof or esters thereof, nitriles, sulphur, sulphur halides, mercaptans, thioethers, thiocarboxylic acids, amines or salts thereof, quarternary ammonium salts and iodine. Examples of individual compounds are: water, methanol, ethanol, (iso)propanol, butanol, chloroethanol, formaldehyde, acetaldehyde, butyraldehyde, benzaldehyde, acetaldehyde dimethyl acetal, acetone, methyl ethyl ketone, benzophenone, acetic acid, chloroacetic acid, dichloroacetic acid, methoxyacetic acid, propionic acid, caproic acid, acetyl or propionyl chloride, dimethylacetamide, chloroacetamide, ethyl acetate, methyl butyrate, acetonitrile, propionitrile, capronitrile, benzonitrile, potassium formate, sodium acetate, potassium chloroacetate, calcium propionate, tin butyrate, sulphur dichloride, butylmercaptan, thiophenol, dimethyl sulphide, dibutyl sulphide, dibutyl disulphide, diphenyl sulfide, thioacetic acid, dimethylamine, ethylamine, butylamine, pyridine, picoline, quinoline, the salts of the amines mentioned, tetramethylammonium chloride, tetraethylammonium chloride and $I_2$.

These co-catalysts are added in an amount of 0.01 to 50% by weight, preferably 0.02–20% by weight, relative to the weight of the zeolite catalyst used. The amount of the co-catalyst depends in part on the polarity of the substance chosen, is usually very variable, but is used advantageously in the lower range, for example in amounts of 0.02–2% by weight.

The process according to the invention can be carried out in the presence or absence of an additional solvent. These solvents have to be resistant to the halogenating agents used; suitable examples are: hydrocarbons or halohydrocarbons such as petroleum ether, methylene chloride, chloroform, carbon tetrachloride, 1,1,1-trichloroethane, 1,2-dichloroethane, perchloroethane, perchloroethylene, lower carboxylic acids such as acetic acid and others known as inert to one skilled in the art. However, in a preferred manner, the reaction is carried out in the melt of the biphenyl to be reacted, thus simplifying the workup of the reaction batch. Furthermore, the reaction according to the invention can be carried out in the gas phase. However, it is preferred to carry it out in the liquid phase.

Furthermore, the reaction can be carried out continuously or batchwise, at atmospheric pressure, reduced pressure or superatmospheric pressure; the pressure is not critical for the course of the process according to the invention and is only of importance, for example, if it is desired to carry out the reaction at an elevated temperature using a highly volatile solvent. In this case, it is advantageous to use the internal pressure of the system.

The process according to the invention can be carried out in a wide temperature range, for example at 0° to 300° C., preferably 30° to 180° C., particularly preferably at 50° to 150° C.

The process according to the invention is carried out, for example, by melting biphenyl with stirring or dissolving it in one of the solvents mentioned in the case of a batchwise operation. The zeolite catalyst is then added in powdered form and 2 mol of the halogenating agent are then passed into the liquid phase at the reaction temperature at the rate at which it is consumed. For continuous operation, for example, columns in which the zeolite catalyst is arranged in compact form are suitable. The co-catalyst used is generally present in the liquid phase of the melt or the solution. The 4,4'-dihalobiphenyls obtainable according to the invention are isolated and purified by using generally known processes such as distillation, vacuum distillation, recrystallization or chromatographic processes. In many cases the desired 4,4'-isomer has a significantly higher melting point and a significantly lower solubility, compared to any halogenated biphenyls of other substitution patterns, which may also be formed. Triply or even more highly halogenated biphenyls are only formed in minor amounts, for example in an amount of 2% by weight at most, however, in many cases in even smaller amounts. This is a great advantage with respect to occupational safety and environmental pollution because of the toxicity of these more highly halogenated biphenyls and also promotes the economy of the process according to the invention. Biphenyls monosubstituted in the 4- or 4'-position can be recycled into the process according to the invention, which likewise allows increased economy.

The zeolite catalyst remaining either as distillation residue or extraction residue can in general be used again according to the invention without further activation. In the case where after several instances of re-use a decrease in activity is observed, the zeolite catalyst can be re-activated by a conventional process, for example by calcination at an elevated temperature, (for example 400°–600° C.).

EXAMPLES

In Examples 1 to 15 and 24–28, the following zeolites were used:

| Example | Type/cation | SiO2/Al2O3 |
|---|---|---|
| 1 | K-zeolite L | 6 |
| 2 | Na, K-zeolite L | 6.4 |
| 3 | H-zeolite L | 7.5 |
| 4 | H-mordenite | 25 |
| 5 | H-mordenite | 16 |
| 6 | H-mordenite | 18 |
| 7 | K-zeolite Ω | 6.2 |
| 8 | H-ferrierite | 17 |
| 9 | H-ZSM 11 | 65 |
| 10 | H-offretite/H-erionite | 6 |
| 11 | Boron silicate SiO2/B2O3 = | 40 |
| 12 | Na-zeolite X | 2.5 |

-continued

| Example | Type/cation | SiO2/Al2O3 |
|---|---|---|
| 13 | K-zeolite H | 4 |
| 14 | Na/K-zeolite L | 6 |
| 15 | K-zeolite Ω | 6.2 |
| 24 | Na, K-zeolite L | 6.4 |
| 25 | K-zeolite L | 6 |
| 26 | K-zeolite Ω | 6.2 |
| 27 | H-ZSM 5 | 90 |
| 28 | H-ZSM 11 | 65 |

In Comparative Examples I to V, the procedure of Example 1 was repeated, except that instead of the zeolites the following catalysts were used:

| Comparative Examples | Catalyst |
|---|---|
| I | without |
| II | 2 g of FeCl3 |
| III | 2 g of FeCl3 + 2 g of thiophene |
| IV | 7 g of 4,4'-dichlorodiphenyl thioether |
| V | 2.5 g of FeCl3 + 2.5 g of 4,4'-dichlorodiphenyl thioether |

EXAMPLES 1 TO 13

In an apparatus equipped with a stirrer, 77.1 g (0.5 mol) of biphenyl was melted with stirring, while nitrogen was passed through, 15 g of active (activated at 400° C. for 3 hours) zeolite powder was added, and 71 g (1 mol) of Cl2 gas was passed into the mixture at 100° C. over a period of 5 hours. The mixture was maintained at 100° C. for another 30 minutes, the melt was degassed with nitrogen and its composition was determined by gas chromatography.

The results are shown together with those of Examples 14 and 15 and of Comparative Examples I to V in Table 1.

EXAMPLE 14

77.1 g (0.5 mol) of biphenyl are melted under nitrogen with the addition of 15 g of K/Na zeolite L, and then 135 g (1 mol) of sulphur chloride are added dropwise to the melt at 100° C. over a period of 3 hours with stirring. After the evolution of gas has stopped, the mixture is flushed with nitrogen, and the composition of the melt is determined by gas chromatography.

EXAMPLE 15

Example 14 is repeated, except that instead of K/Na zeolite L, 15 g of K zeolite were used.

TABLE 1

| | Monochlorobiphenyl | | Dichlorobiphenyls | | | | | | | Trichlorobiphenyls | | | Balance (partly |
|---|---|---|---|---|---|---|---|---|---|---|---|---|---|
| | 2- | 4- | 2,2'- | * | 2,3'- | 2,4'- | 3,3'- | 3,4'- | 4,4'- | * | * | * | unknown) |
| Comparative example | | | | | | | | | | | | | |
| I | 14.5 | 38.6 | — | 3.57 | — | 0.50 | — | 2.17 | 1.55 | — | — | — | 38.5 Biphenyl |
| II | 18.9 | 7.89 | 11.7 | 4.66 | 5.73 | 20.97 | — | 2.24 | 8.04 | 1.77 | 1.99 | 0.87 | 15.3 |
| III | 22.8 | 10.51 | 11.1 | 4.87 | 5.48 | 21.34 | — | 2.41 | 8.61 | 1.11 | 1.46 | 0.62 | 9.7 |
| IV | 33.90 | 25.96 | 1.26 | 2.71 | 0.48 | 7.45 | — | 1.77 | 5.51 | 0.30 | 0.19 | 0.45 | 7.5 Biphenyl + 12.5 unknown |
| V | 28.43 | 3.53 | 9.53 | 3.18 | 2.95 | 27.82 | — | 0.83 | 16.38 | 1.59 | 0.66 | 0.50 | 0.6 |
| Example | | | | | | | | | | | | | |
| 1 | 6.43 | 3.46 | 2.07 | 1.27 | 1.57 | 16.20 | — | 1.36 | 64.14 | 0.48 | 0.99 | 1.03 | 1.0 |
| 2 | 15.02 | 10.84 | 0.98 | 0.96 | 0.77 | 11.76 | 0.05 | 1.50 | 56.13 | 0.13 | 0.50 | 0.36 | 1.0 |
| 3 | 9.62 | 3.75 | 6.18 | 1.56 | 3.25 | 24.0 | 0.36 | 1.60 | 43.32 | 0.43 | 0.85 | 0.83 | 4.24 |

TABLE 1-continued

| | Monochlorobiphenyl | | Dichlorobiphenyls | | | | | | | Trichlorobiphenyls | | | Balance (partly unknown) |
|---|---|---|---|---|---|---|---|---|---|---|---|---|---|
| | 2- | 4- | 2,2'- | * | 2,3'- | 2,4'- | 3,3'- | 3,4'- | 4,4'- | * | * | * | |
| 4 | 19.15 | 9.53 | 1.54 | 2.42 | 0.85 | 22.20 | 0.17 | 1.70 | 37.88 | 2.40 | — | 0.76 | 1.42 |
| 5 | 16.70 | 3.90 | 2.27 | 1.80 | 1.13 | 25.76 | 0.01 | 1.25 | 42.05 | 2.18 | 0.75 | — | 2.22 |
| 6 | 18.64 | 3.88 | 1.16 | 1.72 | 0.73 | 22.00 | — | 1.50 | 45.90 | 2.34 | — | 0.97 | 1.16 |
| 7 | 20.48 | 1.45 | 2.96 | 1.59 | 1.36 | 23.92 | 0.09 | 1.55 | 44.19 | — | 1.04 | 0.79 | 0.57 |
| 8 | 19.42 | 0.60 | 5.35 | 1.60 | 1.57 | 32.52 | — | 0.84 | 35.25 | 0.90 | 0.57 | — | 1.37 |
| 9 | 21.69 | 0.92 | 3.82 | 2.09 | 2.13 | 29.60 | 0.05 | 2.01 | 33.36 | 1.58 | — | 1.01 | 1.72 |
| 10 | 13.04 | 0.30 | 5.51 | 1.48 | 1.89 | 37.37 | 0.33 | 0.70 | 31.72 | 1.15 | 2.82 | 1.78 | 1.92 |
| 11 | 23.18 | 3.14 | 4.54 | 2.28 | 2.17 | 27.91 | — | 2.00 | 31.42 | 0.53 | 1.32 | 0.80 | 0.80 |
| 12 | 14.89 | 0.68 | 7.80 | 2.24 | 2.99 | 32.98 | 0.03 | 1.28 | 32.14 | 1.45 | 0.45 | 0.95 | 1.1 |
| 13 | 22.10 | 3.16 | 3.13 | 1.26 | 1.23 | 26.30 | — | 1.28 | 39.67 | 0.6 | 0.15 | 0.54 | 0.58 |
| 14 | 11.03 | 6.94 | 0.49 | 0.39 | 0.39 | 10.93 | — | 1.04 | 67.05 | — | 0.15 | 0.14 | 1.45 |
| 15 | 21.34 | 1.46 | 3.04 | 1.14 | 1.28 | 24.23 | — | 1.41 | 42.87 | — | 0.53 | 0.62 | 2.08 |

*unknown position of substitution

EXAMPLES 16 TO 20

Example 1 was repeated, except that together with 15 g of catalyst zeolite K-L, the following additives were used.
Example 16—2 g of chloroacetic acid
Example 17—2 g of chloroacetyl chloride
Example 18—1 g of water
Example 19—2 g of sodium chloroacetate
Example 20—2 g of potassium acetate
The results are summarized in Table 2.

EXAMPLES 21 TO 23

Example 1 was repeated using 15 g of K/Na zeolite L (according to Example 2), except that different reaction temperatures were employed:
Example 21—70° C.
Example 2—100° C.
Example 22—120° C.
Example 23—150° C.
The results can be seen from Table 3.

TABLE 2

| | Product composition in % (details analogously to Table 1) | | | | | | | | | |
|---|---|---|---|---|---|---|---|---|---|---|
| | Monochlorobiphenyl | | Dichlorobiphenyl | | | | | | | |
| Example | 2- | 4- | 2,2' | * | 2,3' | 2,4' | 3,3' | 3,4' | 4,4' | Balance |
| 16 | 2.76 | 3.58 | 0.39 | 0.71 | 0.28 | 7.93 | — | 0.78 | 81.76 | 1.81 |
| 17 | 9.96 | 3.79 | 1.30 | 1.46 | 0.96 | 13.15 | — | 1.69 | 66.33 | 1.63 |
| 18 | 10.23 | 1.22 | 2.65 | 1.28 | 1.71 | 16.79 | — | 1.76 | 62.03 | 2.33 |
| 19 | 4.20 | 10.97 | 0.58 | 0.86 | 0.40 | 9.88 | — | 1.12 | 70.39 | 1.60 |
| 20 | 3.80 | 1.36 | 1.39 | 0.97 | 0.93 | 13.54 | — | 1.24 | 74.76 | 2.01 |

*unknown position of substitution

TABLE 3

Temperature dependency of biphenyl chlorination; product composition in % (details analogously to Table 1)

| Example/ temperature | Monochlorobiphenyl | | Dichlorobiphenyls | | | | | | | Trichlorobiphenyls | | | Balance |
|---|---|---|---|---|---|---|---|---|---|---|---|---|---|
| | 2- | 4- | 2,2' | * | 2,3' | 2,4' | 3,3' | 3,4' | 4,4' | * | * | * | |
| 21 70° C. | 9.303 | 9.523 | 1.090 | 0.831 | 0.714 | 13.853 | 1.054 | 59.699 | 0.479 | 0.822 | 0.592 | 2.040 | |
| 2 100° C. | 15.023 | 10.840 | 0.981 | 0.958 | 0.770 | 11.760 | 1.503 | 56.130 | 0.132 | 0.500 | 0.355 | 1.048 | |
| 22 120° C. | 8.559 | 0.662 | 3.094 | 1.315 | 2.106 | 19.479 | 1.807 | 59.371 | 0.484 | 1.066 | 1.048 | 1.009 | |
| 23 150° C. | 5.305 | 0.409 | 4.414 | 1.533 | 3.010 | 23.186 | 1.760 | 53.713 | 0.991 | 1.633 | 1.803 | 2.243 | |

*unknown position of substitution

EXAMPLE 24

77.1 g (0.5 mol) of biphenyl were melted analogously to Example 1 in the presence of 15 g of Na/K zeolite L; 159.8 g (1 mol) of Br2 were then added dropwise to the melt at 100° C. over a period of 8 hours. Stirring was continued for another 30 minutes, the melt was flushed for 30 minutes by passing through nitrogen, and the composition was determined by gas chromatography: the conversion was 100%, the selectivity for 4,4'-dibromobiphenyl 75% and that for 4-monobromobiphenyl 16.5%.

EXAMPLES 25 TO 28

Example 24 was repeated using further zeolites. The conversion, relative to the biphenyl used, was in each case 100%. The zeolites used and the selectivities obtained can be seen from the following list:

| Example | Catalyst | [S] 4,4'-dibromo- | [S] 4-monobromo-biphenyl |
|---|---|---|---|
| 25 | K-L | 78.9 | 11.0 |
| 26 | K-Ω | 81.5 | 8.8 |
| 27 | H-ZSM 5 | 66.8 | 16.5 |
| 28 | H-ZSM 11 | 69.5 | 13.9 |

What is claimed is:

1. In a process for the preparation of 4,4'-dihalobiphenyl of the formula

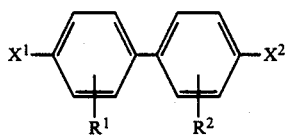

by catalyzed halogenation of a biphenyl of the formula

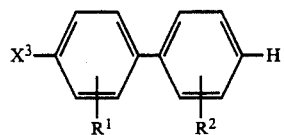

in which the formulae $X^1$ and $X^2$ independently of one another stand for chlorine, bromine or iodine, $X^3$ stands for hydrogen, chlorine, bromine or iodine, and $R^1$ and $R^2$ independently of one another denote hydrogen, $C_1$–$C_4$-alkyl, $C_1$–$C_4$-alkoxy, hydroxyl, fluorine, chlorine or bromine, the improvement comprising reacting the biphenyl with an halogenating agent selected from the group consisting of $Cl_2$, $Br_2$, $I_2$, $SO_2Cl_2$, $SO_2Br_2$, N-chloro- and N-bromosuccinimide, bromine fluoride and bromine chloride in the presence of 1 to 100% by weight relative to the weight of biphenyl reacted of at least one zeolite of the formula $$M_{m/z}[mMe^1O_2 \cdot nMe_2] \cdot qH_2O$$

in which
M denotes an exchangeable cation,
Z denotes the valence of the cation,
$Me^1$ and $Me^2$ represent the elements of the anionic skeleton,
n/m denotes the ratio of the elements and adopts a value of at least 1 and
q denotes the amount of the water absorbed, wherein the zeolites have pore sizes of at least 5 A the halogenation being conducted at from 0° to 300° C.

2. The process according to claim 1, in which $Me^1$ is aluminum.

3. The process according to claim 1, in which $Me^2$ is silicon.

4. The process according to claim 1, wherein the zeolites are selected from faujasite, L, offretite, gmelinite, cancrinite, H, ZSM 12, ZSM 25, zeolite α, ferrierite, ZSM 5, ZSM 11, heulandite, ZSM 22, ZSM 23, ZSM48, ZSM 43, ZSM 35, FSH-3, zeolite, ZSM 38, CSZ-1, ZSM 3, ZSM 20, mordenite, zeolite Q, boron silicate.

5. The process according to claim 4, wherein that the zeolites used are those of the structure type mordenite, ferrierite, H, L, Q, ZSM5 or ZSM 11.

6. The process according to claim 5, wherein the zeolites used are those of the structure type Q or L.

7. The process according to claim 6, wherein zeolites of the structure type Q or L are used in which the exchangeable cations are ions of hydrogen, sodium, potassium or mixtures thereof.

8. The process according to claim 7, wherein the exchangeable cations are ions of sodium, potassium or mixtures thereof.

9. The process according to claim 8, wherein the exchangeable cations are those of potassium.

10. The process according to claim 8, wherein 5–50% by weight of zeolite are used, relative to the weight of biphenyl to be reacted.

11. The process according to claim 11, wherein 20–30% by weight of zeolite are used, relative to the weight of biphenyl to be reacted.

12. The process according to claim 1, wherein the reaction is carried out in the presence of co-catalyst selected from the group: water, alcohols, aldehydes or acetals thereof, ketones, carboxylic acids or salts thereof, halides thereof, amides thereof or esters thereof, nitriles, sulphur, sulphur halides, mercaptans, thioethers, thiocarboxylic acids, amines or salts thereof, quaternary ammonium salts or iodine.

13. The process according to claim 12, wherein the reaction is carried out in the presence of 0.01–50% by weight of co-catalyst, relative to the weight of the zeolite catalyst used.

14. The process according to claim 13 wherein 0.02–20% by weight of co-catalyst are used, relative to the weight of the catalyst used, 15. The process according to claim 1, wherein the reaction is carried out in the melt of biphenyl without a further solvent.

16. The process according to claim 1, wherein unsubstituted biphenyl or a 4-monohalo derivative thereof is used.

17. The process according to claim 1, wherein $X^1$ and $X^2$ independently of one another stand for chlorine or bromine and $X^3$ stands for hydrogen, chlorine or bromine.

* * * * *

UNITED STATES PATENT AND TRADEMARK OFFICE
CERTIFICATE OF CORRECTION

PATENT NO. : 4,950,817

DATED : August 21, 1990

INVENTOR(S) : Botta et al.

It is certified that error appears in the above-identified patent and that said Letters Patent is hereby corrected as shown below:

Col. 10, line 3   Delete " FSH-3 " and substitute -- PSH-3 --

Col. 10, line 22  After " claim " delete " 11 " and substitute -- 10 --

Signed and Sealed this

Fourteenth Day of July, 1992

Attest:

DOUGLAS B. COMER

Attesting Officer     Acting Commissioner of Patents and Trademarks